(12) United States Patent
Kritzler et al.

(10) Patent No.: US 7,244,554 B2
(45) Date of Patent: Jul. 17, 2007

(54) ENZYME DETECTION AND MEASUREMENT

(75) Inventors: Steven Kritzler, Cronulla (AU); Alex Sava, Paddington (AU)

(73) Assignee: Novapharm Research (Australia) Pty Ltd., Rosebery (AU)

( * ) Notice: Subject to any disclaimer, the term of this patent is extended or adjusted under 35 U.S.C. 154(b) by 137 days.

(21) Appl. No.: 10/311,861

(22) PCT Filed: Jun. 20, 2001

(86) PCT No.: PCT/AU01/00728

§ 371 (c)(1),
(2), (4) Date: Apr. 16, 2003

(87) PCT Pub. No.: WO01/98532

PCT Pub. Date: Dec. 27, 2001

(65) Prior Publication Data

US 2003/0166035 A1    Sep. 4, 2003

(51) Int. Cl.
*C12Q 1/00* (2006.01)
(52) U.S. Cl. .................................. 435/4; 435/288.7
(58) Field of Classification Search ............... 435/4, 435/18, 23, 183, 975, 287.8, 287.9, 288.7; 422/55, 57, 60, 61
See application file for complete search history.

(56) References Cited

U.S. PATENT DOCUMENTS

| 4,144,306 A | * | 3/1979 | Figueras ....................... 422/56 |
| 4,767,702 A | | 8/1988 | Cohenford |
| 4,889,797 A | * | 12/1989 | Amano et al. .................. 435/4 |
| 5,418,142 A | * | 5/1995 | Kiser et al. .................... 435/14 |
| 5,571,684 A | * | 11/1996 | Lawrence et al. ............. 435/18 |

FOREIGN PATENT DOCUMENTS

| EP | 0 454 046 A2 | 10/1991 |
| EP | 0 852 336 A1 | 7/1998 |
| EP | 0884393 B1 | 5/2003 |
| JP | 1137997 A | * 5/1989 |
| JP | 0 884 393 A1 | * 12/1998 |
| JP | 0 884 393 B1 | * 5/2003 |
| SU | 1178761 A | 9/1985 |
| WO | 85/01747 | 4/1985 |
| WO | 92/13966 | 8/1992 |
| WO | 96/15255 | 5/1996 |
| WO | WO 00/71167 A1 | 11/2000 |
| WO | WO 01/71025 A1 | 9/2001 |

OTHER PUBLICATIONS

Levenson R. A Collagen Film Microassay for Tissue Collagenase. Analytical Biochemistry 76, 579-588, 1976.*
Carnahan et al., "Enzymatic Characterization of Three *Aeromonas* Species Using API Peptidase, API "Osidase," and API Esterase Test Kits", Diagn Microbiol Infect Dis. 1988:10:p. 195-203.
Zhang et al., "2-Nitro-5-(6-bromohexanoylamino)benzoic Acid Test Paper Method for Detecting Microoraganisms Capable of Producing Cephalosporin Acylases", Analytical Biochemistry 196, 1991, p. 201-206.
Levenson, Richard, "A Collagen Microassay for Tissue Collagenase," Analytical Biochemistry, Academic Press (New York, NY), pp. 579-588, (Aug. 13, 1976).
Johnson-Wint, Barbara, "A Quantative Collagen Film Collagenase Assay for Large Numbers of Samples," Analytical Biochemistry, Academic Press (New York, NY), vol. 104 (No. 1), pp. 175-181, (Sep. 10, 1979).

* cited by examiner

*Primary Examiner*—Ralph Gitomer
(74) *Attorney, Agent, or Firm*—Pillsbury Winthrop Shaw Pittman LLP

(57) ABSTRACT

A unitary single use analytic device for detecting an enzyme in a liquid. The device comprises a support structure for manual manipulation and a composition associated therewith which is responsive to the enzyme in such a way as to cause a change in appearance of the device. The device may be adapted for detecting an enzymes from a plurality of classes by having compositions selectively responsive to an enzyme of one class, each responding in such a way as to cause a change in appearance of the device indicative of the presence of an enzyme of a respective class. Also disclosed is a method for estimating the activity of an enzyme in a liquid comprising the steps of inserting a test strip of the present invention into the liquid and measuring the time taken from the moment of insertion until a predetermined change in appearance of the test strip is observed, or noting the appearance of the strip after predetermined time.

27 Claims, 2 Drawing Sheets

ENZYME DETECTION AND MEASUREMENT

This application is the National Phase of International Application PCT/AU01/00728 filed Jun. 20, 2001 which designated the U.S. and that International Application was published under PCT Article 21(2) in English.

TECHNICAL FIELD

The present invention relates to apparatus for measuring the activity of an enzyme or a combination of enzymes and to methods of use of the apparatus.

BACKGROUND ART

Any discussion of the prior art throughout the specification should in no way be considered as an admission that such prior art is widely known or forms part of common general knowledge in the field.

Living cells produce a series of catalytic agents the purpose of which is to accelerate the reactions that occur under the conditions that occur in living matter. These biocatalysts are called enzymes They are proteins that speed up certain chemical reactions without being themselves affected by the reaction. They are now manufactured on a large scale and used for many purposes.

Enzymes are widely used in industrial processes, food processing and manufacturing, and in household products. For example they have been used in such household products as laundry detergents to assist in digestion of soiling of biological origin, in dishwashing detergents to assist in digestion/removal of food scraps. They are widely used in manufacturing industries for example in tanning of leather, dewooling of fleeces, manufacture of cheeses, of paper, of bread and in many other industries. Enzymes have also been employed in hospitals, medical, dental practices, and the like to assist in digestion and removal of biological contamination from surgical instruments and paraphernalia.

A number of assay methods have been proposed to determine the presence of an enzyme, and to quantify its activity. Generally this involves the conduct of sophisticated and always time consuming chemical assays which need to be conducted by skilled analysts. Annexed hereto and marked annexure 1 is a typical method for determining the proteolytic activity of protease and based on a USP method. The method requires a spectrophotometer and other apparatus, reagents (some of which must be made up fresh daily) and a skilled technician to perform the work. The procedure cannot be completed in less than about 2 hrs.

It would be useful to have means for quickly detecting whether or not a particular enzyme or class of enzymes was present in a sample of a composition. It is also often important to know the degree of activity of one or more enzymes in a system and it would be desirable to have a relatively quick, simple and inexpensive assay method, and preferably one which could be conducted by relatively unskilled persons.

In recent years a large number of test strips have been developed which employ immobilized enzymes to detect an analyte of interest in a sample, for example to measure glucose in a blood sample or of blood in fecal material. Many of these devices require complex amperometric measuring devices to provide a read out and are of relatively complex and costly construction. While such devices employ enzymes, they do not provide a measure of the activity of an enzyme nor an indication of its presence in an analyte.

It is an object of the invention to provide a means of enzyme detection and/or activity assay which avoids or at least ameliorates one or more disadvantages of the above discussed prior art, or provides a commercially useful alternative.

DESCRIPTION OF THE INVENTION

According to one aspect the invention provides a unitary single use analytic device for detecting an enzyme in a liquid at a suitable temperature, said device comprising a support structure for manual manipulation and a composition associated with the support structure, the composition being responsive to the enzyme in such a way as to cause a change in appearance of the device due to digestion of at least a part of a layer of a composition associated with said support structure to reveal an underlying stratum which is of a different appearance from the layer digested.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

In preferred embodiments of the invention the device consists of a support structure in the form of a test strip adapted to be dipped or inserted by hand into a liquid to be tested for the presence of an enzyme or to assess its activity. Desirably the support is an inert carrier such as a sheet of plastic or the like although for some embodiments a sheet of paper or paperboard may be an acceptable support structure. Other supports may be used, for example of glass, metal, ceramic or composites. The support may also be in the form of a dispersion such as polymeric beads or inorganic particles. The associated composition is preferably coated or printed onto the support and may for example be, or include, a composition selectively digestible by an enzyme of a particular class of enzyme. For example the associated composition may be, or include, a protein selectively digestible by an enzyme of the class of proteases; or it may be, or include, a lipid digestible by enzymes of the class of lipases; or it may be, or include, a cellulose digestible by enzymes of the class of cellulases, and so on, or a plurality of such compositions may be associated with a single support. The composition may include a binder if necessary to maintain association with the support, or in the case of an enzyme digestible composition which can itself be formed into a cohesive sheet may be adhered as a sheet to the support.

In embodiments of the invention interaction between the composition and an enzyme in a liquid being tested results in a change in appearance of the test strip, for example the composition may change colour, or the composition may be digested to reveal an underlying stratum of a different appearance. Various ways in which a change in the appearance of the device in response to detection of an enzyme can be accomplished are discussed in more detail hereinafter.

In one highly preferred form of the invention the composition is enzyme digestible and includes a fine dispersion of a solid (for example, barium sulphate) of which a layer at or near an exposed surface, or a portion of that layer, is coloured. An enzyme which is effective to digest the composition, releases the coloured particles in the coloured layer, which fall free of the test strip. Since the coloured layer at or near the surface is of a different appearance than the underlying remainder (which in the case of a barium sulphate dispersion is opaque white), digestion of the surface layer results in a visible color change in the strip.

In preferred embodiments quantitative measurement of enzyme activity may be undertaken by measuring the time from the moment of immersion of the test strip until a change in appearance is observed and comparing the time with a reference chart or sample. In other embodiments the degree of change in appearance which takes place in a predetermined time interval is used to indicate enzyme activity.

BRIEF DESCRIPTION OF THE DRAWINGS

Various embodiments of the invention will now be described by way of example only with reference to the accompanying drawings wherein.

BEST MODES FOR CARRYING OUT THE INVENTION

Figure 1:
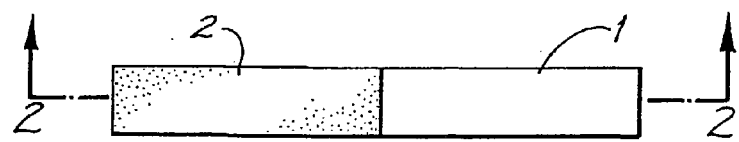
FIG. 1 shows a schematic plan view of a first embodiment according to the invention.
Figure 2:
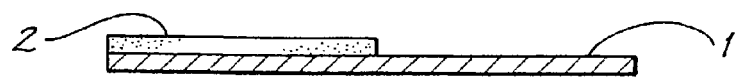
FIG. 2 shows a cross-section along line 2-2 of FIG. 1.

A first embodiment of the invention is shown in FIGS. 1 and 2 in which there is provided a simple form of device. The device of FIG. 1 is a test strip intended for single use in detecting a protease followed by disposal. The device consists of a support structure 1 which in the illustrated example is in the form of a strip but which need not be rectangular in shape, nor need it necessarily be flat. In the present example support 1 is of plastic and is shaped to assist in manual manipulation having regard to the manner of its intended use. Support structure 1 is coloured, (for example support structure 1 may be a blue coloured plastic) and is associated with an enzyme digestible composition 2 by being coated with an adherent layer of predetermined thickness of the composition. Composition 2 is a gelatin in which is dispersed finely divided barium sulphate yielding an opaque white composition. Prior to use of the test strip the blue colour of support structure 1 is obscured by the overlying coating of white composition 2. In use the strip is inserted into a liquid containing a protease enzyme the activity of which is to be assayed and which is at a known temperature. A stopwatch is used to measure the time from the moment of insertion of the strip into the liquid until the layer of composition 2 is digested as evidenced by the change in appearance of the coated portion of the test strip from the white colour of composition 2 to the blue colour of the support 1. The stopwatch is then stopped and the activity of the enzyme assessed by reference to pre-calibrated tables of time versus activity for the predetermined thickness of that composition. Those skilled in the art will appreciate that enzyme activity and the rate of digestion of a substrate by an enzyme are temperature dependant and that the sample must either be preconditioned to a specified suitable temperature or the temperature of the solution must be measured and a temperature adjustment factor applied. In the embodiment of FIG. 1 it is not necessary for the whole support structure to be covered by the associated composition. However in this embodiment it is important to precisely and reproducibly control the thickness of coating of composition 2 on support 1 if the strip is to be used for estimating enzyme activity.

If desired, the strip may be accompanied by a calibration chart (the two forming a kit), showing the user the end point colour of the support, or an exposed uncovered portion of support may be left to facilitate this colour comparison. The solid suspension if employed need not be barium sulphate but may be a silica, titanium dioxide, metal colloid, or other opacifier.

The support need not be coloured. Support 1 may be a transparent film and a light beam and photodiode or the like together with an optional timing circuit may be used to monitor the digestion of the composition and register the endpoint (when the light beam passes through carrier and composition layer) and time the digestion. In other embodiments the digestible coating when digested may reveal underlying indicia printed on the carrier, for example the word "protease" or an abbreviation such as "P".

The above described embodiment is intended to detect and measure the activity of proteases. However other compositions may be used for the detection of enzymes from other enzyme classes. For example a composition utilizing a cellulose substrate may be used to detect enzymes of the cellulase class, compositions containing lipids may be used to detect enzymes of the lipase class, compositions containing amylopectin may be used to detect enzymes of the amylase class and so on.

Figure 3:
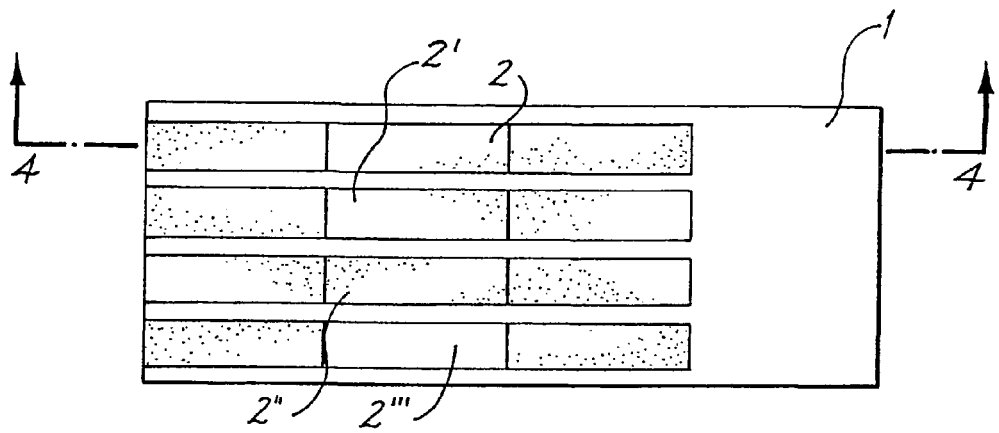
FIG. 3 shows a schematic plan view of a second embodiment according to the invention.
Figure 4:
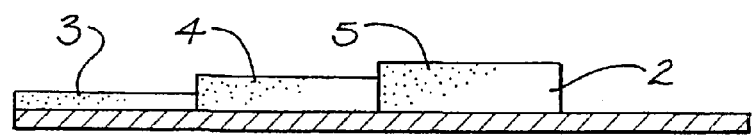
FIG. 4 shows a cross-section along line 3-3 of FIG. 3.

A more highly preferred embodiment is shown in FIGS. 3 and 4. The device of FIG. 3 differs from that of FIG. 1 in that a single support structure 1 is associated with several different enzyme digestible compositions, each of which is specific to one or a class of enzymes, so that the strip is able to test for the presence of more than one enzyme and to assay several different classes of enzyme coexisting in a mixture. In that case the different compositions may be visually distinguished from each other for example by colour, or they may be of the same colour but occupy visually distinct parts of the support. They may have the same or different underlying colours. or indicia.

Although in preferred embodiments the composition associated with the support is applied to the support as a coating of predetermined uniform thickness and time of digestion is measured, in less desirable embodiments a coating of continuously varying or stepped variable thickness may be used, and the thickness digested in a given time assessed. In that case a different value may be revealed beneath each thickness step and the highest value revealed within a predetermined time would be indicative of the activity With reference to FIG. 3 there is shown by way of example a schematic drawing of a device according to the invention in the form of a test strip consisting of a support structure 1 being a cellulose acetate film, coated with an overlying layer or stripe of first composition 2, a layer of a second composition 2', a layer of a third composition 2", and a layer of a fourth composition 2''', each of compositions 2, 2', 2", 2''' is selectively digestible by a respective enzyme or class of enzyme different from each other.

Each overlying layer or strip 2, 2', 2", 2''' is selectively digestible by a different enzyme or class of enzyme from each other. Layer 2 is a protein layer, layer 2' is a lipid layer, layer 2" is a cellulose, and layer 2''' is a carbohydrate. More specifically, in the present example layer 2''' is amylopectin which is digestible by amylase but not cellulase. Layers 2, 2', 2", 2''' are disposed as parallel strips and may be contiguous (as shown in FIG. 1) or may be spaced apart on substrate 1.

As shown in the cross-section of FIG. 2, strips 2, 2', 2", 2'" are not of uniform thickness but are progressively stepped in thickness at levels 3, 4, 5 etc. There may be more or fewer changes in level or the thickness may be continuously increased.

The coatings may be applied to the substrate by any suitable process, e.g. printing using rotogravure, screen printing, ink jet printing, knife coating, or other means suitable for depositing layers of predetermined thickness.

Each of the compositions is made opaque by incorporating therein prior to coating the support a finely dispersed suspension of barium sulphate. The dispersion hides the underlying support. The support may be transparent, coloured, or covered with a coloured layer. The colour of the support is desirably different under each of compositions 2, 2', 2", 2'". There may be indicia under each step 3, 4, 5 in composition thickness. Alternatively the compositions may be dyed or coloured so that the thickness remaining after a predetermined time can be judged by comparison with a tint chart.

In a third embodiment described with reference to FIGS. 5 and 6. A paddle shaped support 1 has a portion 11 adapted for immersion and a handle portion 12. Portion 11 is coated with a plurality of enzyme digestible compositions 2, 2', 2" each of which is selectively digestible by an enzyme of a different class. Each of compositions 2, 2', 2 are coloured on or in a surface layer. In one variation of this technique shown in FIG. 6 this is accomplished by printing or coating an ink 6 for example in a dot or grid pattern onto the exposed surface of compositions 2, 2', 2". Ink 6 is insoluble in the enzyme containing liquid to be tested. A suitable ink employs a water insoluble pigment, for example D & C violet No.2. When portion 11 is inserted into a liquid containing a suitable enzyme, responsive composition 2 is digested and as the liquid interface is consumed, ink 6 is released and falls away producing a change in appearance.

Figure 5:
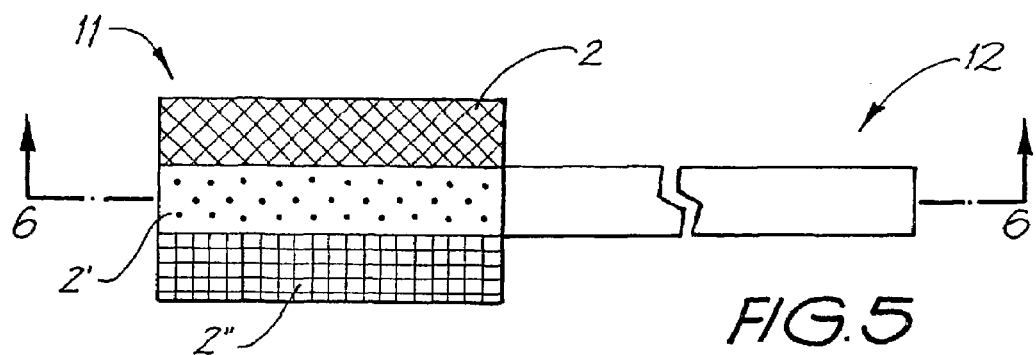
FIG. 5 shows a schematic plan view of a third embodiment according to the invention.
Figure 6:
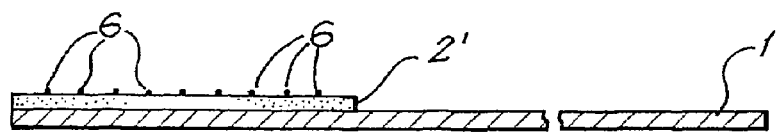
FIG. 6 shows a cross-section along line 5-5 of FIG. 5.
Figure 7:
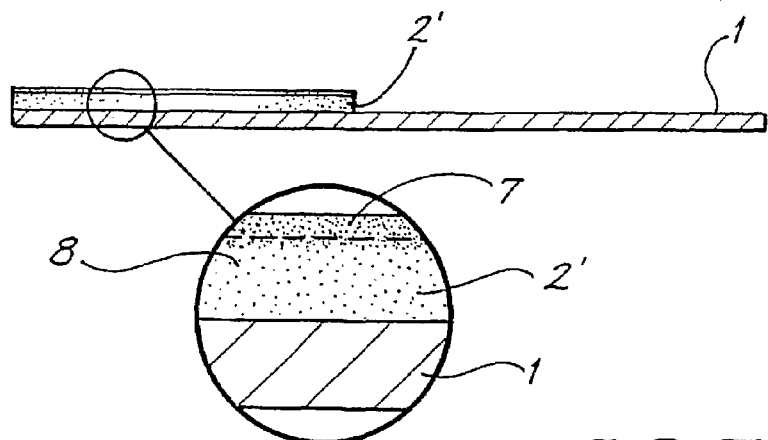
FIG. 7 shows a preferred variation of the third embodiment in a cross-section similar to that of FIG. 6.

A preferred form of the third embodiment appears the same as that of FIG. 5 in plan but is shown in FIG. 7 in elevation. In this form compositions 2, 2', 2" contain a suspension of a finely divided solid, for example, barium sulphate. An ink or dye is applied to the surface of composition 2 in a measured amount for example by ink jet printing. The ink penetrates compositions 2, 2', 2" and colours a thin layer 7 of the suspended solid at or near the surface. When portion 11 is inserted vertically into a solution containing an enzyme, a composition 2 responsive to that enzyme is digested and as the composition at the liquid interface is consumed the coloured powder of layer 7 falls away under gravity or diffusion producing a change in appearance because strata 8 underlying coloured layer 7 is white. Of course a non-white solid could be used as the suspension. If desired a coloured solid could be trapped on or in a surface layer of composition 2 by other means. For example light sensitive solid particles could be changed in colour at or near the surface by means of exposure to light. It has been found that embodiments utilizing an enzyme digestible composition in which a surface layer is of a different appearance from an underlying stratum avoids the need for accurate and reproducible control of coating thickness of the composition on the support. It is much easier to colour a thin layer reproducibly than to produce a coating of predetermined thickness and this gives suprisingly reproducible and accurate end point indication. Barium sulphate is preferred as a dispersion for this purpose because of its high specific gravity.

In the embodiments so far described compositions associated with the support have all been of a kind which are selectively digestible by an enzyme of a particular class. However the composition need not be enzyme digestible. The composition may be selected to react with the enzyme to produce a product, either directly or via one or more reaction intermediates or mediators such as to produce a colour change. For example composition 2 may comprise a porous binding medium in which is immobilized a sucrose together with an electron transfer mediator such as ferricyanide, ferrocene, methylene blue, p-benzoquinone, 2,6-dichlorophenyolindophenol, pyocyanine or thioneine. In the presence of a glucose oxidase in a liquid the activity of which is to be measured, the glucose in the device is oxidised to gluconic acid and the mediator is reduced for example from ferricyanide to ferrocyanide. Reactions of this type may be accompanied by a colour change or used to bring about a colour change in a suitable redox indicator which would indicate the activity of the oxidase. Other substrate/mediator systems can be used for other enzyme classes.

EXAMPLES

Coating compositions for use in the invention are given below by way of example only:

1 Protease Digestible Coating

| Liquid Gelatin (Hipure from Norland Products) | 30% |
|---|---|
| Titanium oxide | 60% |
| Glycerol | 10% |

2. Cellulase Digestible Coating

| High Molecular Weight Carboxymethyl cellulose(Tylose 30.000) | 6% |
|---|---|
| Titanium oxide powder | 10% |
| Distilled water | q.s 100% |

3 Lipase Digestible Coating

| PNPvalerate | 0.4% |
|---|---|
| Glycerine monostearate | 0.3% |
| Titanium oxide powder | 10% |
| Hot water | q.s. 100 |

4 Amylase Digestible Coating

| Mixture of Agarose and Agaropectin (supplied by Oxoid, code No. L28) | 1.5% |
|---|---|
| Titanium oxide powder | 10% |
| Water | q.s. 100 |

The mixture sets at 32-35° C. and may be deposited as thin layer.

Amylopectin or any other long-chain polysaccharide insoluble in cold water may be used in the formulation instead of agarose/agaropectin mixture 5 Composition for Detecting Products/Byproducts of Reaction with a Protease The method is based on detecting polypeptide bonds of protein fragments soluble in cold water resulting from breakdown of cold water-insoluble proteins in substrate: The strip may include two spatially separated parts, one with the substrate and the other with the reagent, or alternatively the parts may be combined in a matrix.

| Substrate: | Gelatin layer as above | |
|---|---|---|
| Reagent: | 2,4-Dinitrofluorobenzene (DNF) | 1%; |
| | Triethanolamine | 1% |
| | PVP-VA 535 co-polymer | 10% |
| | (supplied by ISP Corp) | |
| | Ethanol | 88% |

When subjected to protease action, gelatin breaks down to smaller water soluble polypeptides that react with DNF forming bright yellow colour.

6 Composition for Detecting Products/Byproducts of Reaction with an Amylase

| Agarose/Agaropectin mixture | 1% |
|---|---|
| Copper tartrate | 1% |
| Triethanolamine | 1% |
| PVP-VA co-polymer | 10% |
| Ethanol | q.s. 100 |

7 Composition for Detecting Products/Byproducts of Reaction with a Cellulase

| Tylose 30000 | 2% |
|---|---|
| Copper tartrate | 1% |
| Triethanolamine | 1% |
| PVP-VA co-polymer | 10% |
| Ethanol | q.s. 100 |

Those skilled in the art will be able to select other suitable substrates based on the teaching herein.

The features of one embodiment may be combined with those of another. As will be apparent from the teaching hereof the compositions for use in the invention may be formulated in different ways and combined with each other and with suitable substrates in many different forms without departing from the inventive concept herein disclosed.

Annexure 1

1.0. Scope and Purpose:

This method is to determine the proteolytic activity in Enzyme Preparations and Detergents (Azocasein Substrate)

2.0. Unusual Safety Precautions:
　None 3.0. Principle of Method:

A protease is allowed to hydrolyze azocasein for 30 minutes at 40° C. Undigested protein is precipitated with trichloroacetic acid and the quantity of digested product is determined by spectrophotometry.

4.0. Apparatus:
　4.1 Spectrophotometer
　4.2 pH Meter
　4.3 Water Bath at 40° C.±0.5° C.
　4.4 Timer
　4.5 Vortex Mixer
　4.6 16×125 mm test tubes
　4.7 Repeating dispenser, 5 ml capacity
　4.8 Small funnels and filter paper. Whatman No. 3 or equivalent.
　4.9 Displacement 1 ml and 0.1 ml pipettes 5.0. Reagents
　6.1 2.0 M Tris buffer stock solution Dissolve 242 g trishydroxymethylaminomethane (Trizma Base T 1503—or equivalent) in 700-800 deionised water. Adjust pH to 8.5 with 10 N $H_2SO_4$. Adjust volume to 1 litre. This concentrate is to be used at 10 m/100 ml volume for all final dilutions with 0.2 M Tris buffer.

6.2 50% Urea solution

Dissolve 50 g urea (analytical grade) in 50 ml warm deionised water. Adjust volume to 1 litre.

6.3 10% Trichloroacetic acid solution (stop reagent)

Dissolve 100 g trichloroacetic acid (TCA) in 200 ml deionised water. Adjust volume to 1 litre.

6.4 Azocasein (substrate solution)

Make fresh daily—discard any unused substrate
In a 250-ml beaker:
Weigh 0.6 g azocasein (Sigma A-2765)
Add 10 ml 50% urea solution and mix until dissolved.
Add 10 ml 2.0 M Tris buffer stock solution.
Add 30-50 ml deionised water and continue stirring until clear of particles.
Adjust pH to 8.5 using dilute $H_2SO_4$
Adjust volume to 100 ml and mix thoroughly
Keep cool until ready to begin assay.

7.0 Enzyme Samples and Standards

After dissolving an Epizyme Rapid Sample for protease assay, it is strongly recommended that the pH of this solution be checked and, if needed, adjusted to 8.5±0.1 units.

If it is desired to know the exact activity levels of protease in a detergent, the detergent base should be included in the standard solutions unless it is already known that the particular formulation being used has no effect on the protease activity. The concentration of the base detergent should be equal to that used in the sample solution of the detergent containing protease.

The presence in solution of strong chelators such as NTA or EDTA may result in deactivation of the protease over the time period required for preparation of the various materials for the assay. This cause of deactivation can be overcome by adding excess calcium to the sample solutions.

6.0. Procedure
　6.1 Preheat water bath to 40° C.±0.5° C. (approx. 1 hour).
　6.2 Approx. 10 minutes before starting assay, place substrate solution on 40° C. water bath to equilibrate.
　6.3 Incubate the tubes in a 50° C. water bath for 10 minutes.
　6.4 Remove the tubes from the water bath and quickly add 500 µL of colour reaction solution to each tube at approximately equal time intervals. The colour reaction solution should be added to all tubes within one minute. Recap and vortex. Again, be careful not to splash the reaction onto the top of the microcentrifuge tube.
　6.5 Incubate the tubes in a 80° C. water for bath for 20 minutes.
　6.6 Place all tubes in an ice water bath to cool for 15 minutes.
　6.7 Transfer the reaction of all tubes to 1.5 mL cuvettes and read absorbance at 560 nm.

7.0 Calculations

Calculate the mean absorbance for each standard, and sample replicate. Subtract the average blank absorbance reading from each value in order to obtain an average net absorbance reading.

Generate a standard curve of net absorbance vs enzyme concentration for the standards. A correlation coefficient (r) of 20.999 should be obtained.

Calculate the NPC/g value for each LIQUID sample from the standard curve.

NPC/gm=(NPC/mL, value from curve)(stock dilution)) Sample specific gravity g/mL

Calculate the NPC/g granule value for each GRANULAR sample from the standard curve.

NPC/gm=(NPC/mL, value from curve)(stock dilution)) (Stock dissolution conc. Mg/mL) (1 gm/1000 mg)

8.0 Reference:
USP

The invention claimed is:

1. A unitary single use analytic device for detecting an enzyme in a liquid, said device comprising a support structure for manual manipulation and a predetermined thickness of an opaque composition associated with the support structure, the opaque composition containing a finely divided solid dispersion and being responsive to the enzyme in such a way as to cause a change in appearance of the device due to digestion of at least a part of the composition to reveal an underlying stratum which is of a different appearance from the layer digested, wherein digestion of the predetermined thickness is indicative of activity of the enzyme.

2. The unitary single use analytic device according to claim 1, comprising a support structure for manual manipulation, a first opaque composition and a second opaque composition each associated with the support structure, the first opaque composition containing a finely divided solid dispersion and being selectively responsive to an enzyme of a first class and the second opaque composition containing a finely divided solid dispersion and being responsive to an enzyme of a second class, each responding in such a way as to cause a change in appearance of the device indicative of the presence of an enzyme of a respective class and wherein the change in appearance of the device is due to digestion of a layer of a composition associated with said support structure to reveal an underlying stratum which is of a different appearance from the layer digested.

3. The device according to claim 1, wherein the underlying stratum revealed is the support structure or a coating on the support structure.

4. The device according to claim 1, wherein the dispersion is barium sulphate.

5. The device according to claim 1, wherein a change in appearance of the device is due to digestion of a surface layer of the composition whereby a substance captive in or on the surface layer which differs in appearance from an underlying stratum of the composition is released.

6. The device according to claim 5, wherein the substance captive in or on the surface layer is an ink or pigment applied to a surface of the composition.

7. The device according to claim 1, wherein the composition contains a solid dispersion of which at least a surface layer portion is colored differently from a remainder portion.

8. The device according to claim 7, wherein the surface layer portion is colored by application of an ink or dye.

9. The device according to claim 1, wherein a change in appearance is due to a reaction between a component of the composition and the enzyme in the liquid to produce a product of different appearance either directly or via one or more mediators.

10. The device according to claim 1, wherein a time period from insertion of a predetermined portion of the device in the liquid until a predetermined change, if any, in appearance is observed is indicative of an activity of the enzyme.

11. The device according to claim 1, wherein the appearance of the device changes with time after immersion of a predetermined portion of the device in the liquid containing the enzyme and wherein the appearance after a predetermined time is indicative of an activity of the enzyme.

12. The device according to claim 1, wherein the composition is protease digestible.

13. The device according to claim 1, wherein the composition is cellulase digestible.

14. The device according to claim 1, wherein the composition is lipase digestible.

15. The device according to claim 1, wherein the composition is amylase digestible.

16. The device according to claim 1, wherein the composition is oxidase digestible.

17. The device according to claim 1, wherein the composition forms a layer of uniform thickness and is selectively digested in a predetermined time by the enzyme.

18. The device according to claim 1, wherein the composition forms a layer of progressively increasing thickness and is selectively digested in a predetermined time by the enzyme whereby the thickness digested in the predetermined time is indicative of an activity of the enzyme.

19. The device according to claim 1, wherein the composition is a layer increasing in thickness in a plurality of steps of predetermined thickness each of which is selectively digested in a predetermined time according to the step thickness by the enzyme, whereby a number of steps are digested and the number of steps digested in the predetermined time is indicative of an activity of the enzyme.

20. The device according to claim 1, wherein the support structure is formed from a plastic sheet or film.

21. A method for estimating the activity of an enzyme in a liquid comprising the steps of inserting a test strip into the liquid, the test strip comprising a support structure, a predetermined thickness of an opaque composition associated with the support structure, the opaque composition containing a finely divided solid dispersion and being responsive to the enzyme in such a way as to cause a change in appearance of the test strip;

measuring a time period taken from the moment of insertion until a predetermined change in appearance of the test strip is observed; and correlating the predetermined change in appearance with a level of activity of the enzyme;

wherein the composition is enzyme digestible and wherein the change in appearance of the test strip results from a change in appearance at a surface of the composition.

22. The method according to claim 21, wherein the change in appearance of the test strip results from digestion of the composition to reveal the support structure underlying the composition.

23. The method according to claim 21, wherein the change in appearance is a change in transparency of the test strip.

24. The method according to claim 21, wherein the liquid is maintained at a predetermined temperature.

25. The method according to claim 21, wherein the test strip comprises a plurality of compositions on the support structure, each being selectively digestible by an enzyme of a respective class, and the method further includes the step of measuring a time period taken for each composition to change in appearance.

26. A method of estimating the activity of an enzyme comprising the steps of inserting a test strip into a liquid containing the enzyme, the test strip comprising a support structure coated with one or more layers of increasing predetermined thickness of an opaque composition containing a finely divided solid dispersion and digestible by the enzyme at a predetermined activity in a predetermined time, and visually distinguishable from the support structure;

measuring a thickness of the opaque composition digested in a predetermined time; and correlating the thickness of the opaque composition digested in the predetermined time with the predetermined activity of the enzyme.

27. A kit including:

a unitary single use analytical device for detecting an enzyme in a liquid, said device comprising a support structure for manual manipulation and a predetermined thickness of an opaque composition associated with the support structure, the opaque composition containing a finely divided solid dispersion and being responsive to the enzyme in such a way as to cause a change in appearance of the device due to digestion of at least a part of a layer of the composition to reveal an underlying stratum which is of a different appearance from the layer digested, wherein digestion of the predetermined thickness is indicative of activity of the enzyme; and an indicator of the appearance of a predetermined change, if any, in appearance of the device.

* * * * *